(12) United States Patent
Kakehi

(10) Patent No.: US 7,700,745 B2
(45) Date of Patent: Apr. 20, 2010

(54) METHOD FOR SEPARATING CARBOHYDRATE IN GLYCOSIDE-LINKAGE-HAVING COMPOUND, CARBOHYDRATE SEPARATING SYSTEM, CARBOHYDRATE SEPARATING REAGENT KIT, STANDARD SAMPLE FOR CARBOHYDRATE SEPARATION, AND EVALUATION SYSTEM

(75) Inventor: Kazuaki Kakehi, Nara (JP)

(73) Assignee: Japan Science and Technology Agency (JP)

( * ) Notice: Subject to any disclaimer, the term of this patent is extended or adjusted under 35 U.S.C. 154(b) by 422 days.

(21) Appl. No.: 10/546,961

(22) PCT Filed: Jan. 21, 2004

(86) PCT No.: PCT/JP2004/000508

§ 371 (c)(1),
(2), (4) Date: May 17, 2006

(87) PCT Pub. No.: WO2004/077048

PCT Pub. Date: Sep. 10, 2004

(65) Prior Publication Data

US 2006/0211849 A1    Sep. 21, 2006

(30) Foreign Application Priority Data

Feb. 28, 2003    (JP) .............................. 2003-054752

(51) Int. Cl.
*C07H 1/00* (2006.01)
*C07H 3/00* (2006.01)
*C08B 37/00* (2006.01)

(52) U.S. Cl. .................... 536/1.11; 536/124; 536/123.1

(58) Field of Classification Search ................ 536/1.11, 536/124, 123.1
See application file for complete search history.

(56) References Cited

U.S. PATENT DOCUMENTS

| | | | |
|---|---|---|---|
| 5,519,635 A | 5/1996 | Miyake et al. | |
| 6,444,233 B1 * | 9/2002 | Arntzen et al. | 424/725 |
| 2003/0129761 A1 * | 7/2003 | Kakita et al. | 436/94 |

FOREIGN PATENT DOCUMENTS

| | | |
|---|---|---|
| JP | 56-128569 | 9/1981 |
| JP | 06-087904 | 3/1994 |
| JP | 7-83935 | 3/1995 |
| JP | 9-274029 A | 10/1997 |
| JP | 2003-339393 | 12/2003 |
| JP | 2004-144568 | 5/2004 |

OTHER PUBLICATIONS

Calbiochem General Catalog 2002-2003. Catalog No. 362280, "Glycoprotein Deglycosylation Kit," p. 299.*
Definition of "glycoside" from Drug Discovery & Development Magazine online glossary [online], [Retrieved on Jul. 9, 2009]. Retrieved from the internet <http://www.dddmag.com/Glossary.aspx>.*
Definition of "glycoside" from the Merriam Webster Online Dictionary [online], [Retrieved on Jul. 9, 2009]. Retrieved from the internet <http://www.merriam-webster.com/dictionary/glycoside>.*
"Chemical Deglycosylation Strategies" from Sigma-Aldrich [online], [Retrieved on Jul. 7, 2009]. Retrieved from the internet <http://www.sigmaaldrich.com/img/assets/15880/chemical_and_enzymatic_deglycosylation_strategies.pdf>.*
Sakaguchi, H., Watanabe, M., Ueoka, C., Sugiyama, E., Taketomi, T., Yamada, S., Sugahara, K. (2001) Isolation of Reducing Oligosaccharide Chains from the Chondroitin/Dermatan Sulfate-Protein Linkage Region and Preparation of Analytical Probes by Fluorescent Labeling with 2-AminoBenzamide. Journal of Biochemistry, vol. 129, p. 107-118.*
Huang, Y et al., "Microscale Nonreductive Release of O-Linked Glycans for Subsequent Alaysis through MALDI Mass Spectrometry and Capillary Electrophoresis" Analytical Chemistry, vol. 73, No. 24, Dec. 15, 2001.
Karlsson, N.G. et al., "Analysis of O-Linked Reducing Oligosaccharides Released by an In-line Flow System" Analytical Biochemistry 305, on-line publication May 16, 2002.
Office Action issued in corresponding Japanese Patent Application No. 2005-502815 with a mailing date of Apr. 15, 2008, 4 pages.

(Continued)

*Primary Examiner*—Shaojia Anna Jiang
*Assistant Examiner*—Scarlett Goon
(74) *Attorney, Agent, or Firm*—Sheridan Ross P.C.

(57) ABSTRACT

In an in-flow chemical reaction system (A) of the present invention, a sample solution (1) containing glycoprotein is injected into a reaction tube (7) in which an alkaline solution continuously flows. When a mixed solution of the sample solution and the alkaline solution reach a thermostat bath (6), reaction for cleaving a glycoside linkage takes place, thereby separating a carbohydrate chain from glycoprotein. From the solution containing the carbohydrate chain, alkali is removed by using an ion-exchange column (12), so that a fraction of a carbohydrate chain (14) is collected into a sample tube (13). In the in-flow chemical reaction system (A), reaction takes place in minutes, so that reaction time is significantly reduced compared to a conventional method. Thus, a glycoside linkage is readily cleaved with high precision in a short time, thereby separating carbohydrate from a glycoside-linkage-having compound.

5 Claims, 9 Drawing Sheets

OTHER PUBLICATIONS

Kakehi et al., "High-performance capillary electrophoresis of O-glycosidically linked sialic acid-containing oligosaccharides in glycoproteins as their alditol derivatives with low-wavelength UV monitoring," Journal of Chromatography A. 680 (1994) 209-215.

Matsuno et al., "Development of an apparatus for rapid release of oligosaccharides at the glycosaminoglycan-protein linage region in chondroitin sulfate-type proteoglycans," Analytical Biochemistry 362 (2007) 245-257.

Matsuno et al., "Rapid and Sensitive Analysis of O-linked Glycans Using an In-line Flow Glycan-releasing Apparatus," Trends in Glycoscience and Glycotechnology, vol. 20, No. 111 (Jan. 2008) pp. 29-50.

Yamada et al., "Comparative Studies on the Structural Features of O-Glycans between Leukemia and Epithelial Cell Lines," Journal of Proteome Research 2009, 8, 521-537.

Yamada et al., "Rapid and sensitive analysis of mucin-type glycans using an in-line flow glycan-releasing apparatus," Analytical Biochemistry 371 (2007) 52-61.

Yamada et al., "Determination of Tn antigen released from cultured cancer cells by capillary electrophoresis," Analytical Biochemistry 2009, pp. 1-3.

* cited by examiner 1.5m

| TEMPERATURE | UPPER BAND(Abs) | LOWER BAND(Abs) | UPPER BAND(μg) | LOWER BAND(μg) | total |
|---|---|---|---|---|---|
| 50 | 0.245 | 0.035 | 11.23853 | 1.605505 | 12.84404 |
| 60 | 0.201 | 0.042 | 9.220183 | 1.926606 | 11.14679 |
| 70 | 0.162 | 0.05 | 7.431193 | 2.293578 | 9.724771 |
| 80 | 0.164 | 0.069 | 7.522936 | 3.165138 | 10.68807 |
| 90 | 0.121 | 0.083 | 5.550459 | 3.807339 | 9.357798 |

3m

| TEMPERATURE | UPPER BAND(Abs) | LOWER BAND(Abs) | UPPER BAND(μg) | LOWER BAND(μg) | total |
|---|---|---|---|---|---|
| 50 | 0.297 | 0.039 | 7.054632 | 0.926366 | 7.980998 |
| 60 | 0.207 | 0.059 | 4.916865 | 1.401425 | 6.31829 |
| 70 | 0.195 | 0.096 | 4.631829 | 2.280285 | 6.912114 |
| 80 | 0.122 | 0.154 | 2.897862 | 3.657957 | 6.555819 |
| 90 | 0.057 | 0.2 | 1.353919 | 4.750594 | 6.104513 |

5m

| TEMPERATURE | UPPER BAND(Abs) | LOWER BAND(Abs) | UPPER BAND(μg) | LOWER BAND(μg) | total |
|---|---|---|---|---|---|
| 50 | 0.236 | 0.061 | 10.39648 | 2.687225 | 13.0837 |
| 60 | 0.166 | 0.082 | 7.312775 | 3.612335 | 10.92511 |
| 70 | 0.157 | 0.133 | 6.9163 | 5.859031 | 12.77533 |
| 80 | 0.105 | 0.167 | 4.625551 | 7.356828 | 11.98238 |
| 90 | 0.044 | 0.182 | 1.938326 | 8.017621 | 9.955947 |

10m

| TEMPERATURE | UPPER BAND(Abs) | LOWER BAND(Abs) | UPPER BAND(μg) | LOWER BAND(μg) | total |
|---|---|---|---|---|---|
| 50 | 0.142 | 0.078 | 5.107914 | 2.805755 | 7.913669 |
| 60 | 0.111 | 0.103 | 3.992806 | 3.705036 | 7.697842 |
| 70 | 0.058 | 0.16 | 2.086331 | 5.755396 | 7.841727 |
| 80 | 0.048 | 0.177 | 1.726619 | 6.366906 | 8.093525 |
| 90 | 0.038 | 0.116 | 1.366906 | 4.172662 | 5.539568 |

FIG. 7

| structure | m/z [M+H]+ Theoretical | m/z [M+H]+ Determined Standard | m/z [M+H]+ Determined Flow systemA | m/z [M+Na]+ Theoretical | m/z [M+Na]+ Determined Standard | m/z [M+Na]+ Determined Flow systemA |
|---|---|---|---|---|---|---|
| GalNAc-3AB (Mw. 340.3) | 341.3 | 340.5 | 340.4 | 363.3 | — | 362.3 |
| NeuAc2→6GalNAc-3AB (Mw. 631.6) | 632.6 | 630.8 | 630.8 | 654.6 | 652.8 | 652.8 |
| NeuGc2→6GalNAc-3AB (Mw. 647.6) | 648.6 | 647.8 | 647.8 | 670.6 | 668.8 | 668.7 |
| NeuAc2→6GalNAc-3AB, GlcNAc1→3 (Mw. 834.8) | 835.8 | 833.7 | — | 857.8 | 855.7 | 855.6 |
| NeuGc2→6GalNAc-3AB, GlcNAc1→3 (Mw. 850.8) | 851.8 | — | — | 873.8 | 871.7 | 871.6 |

```
C-R8A  CHROMATOPAC    CH=1       DATA=1:@CHRM1.COO       ATTEN= 5      SPEED= 3.0
```

```
C-R8A  CHROMATOPAC CH=1 Report NO.=1    DATA=1:@CHRM1.COO    02 11 28 11:07:16
** CALCULATION REPORT **
CH PKNO   TIME     AREA      HEIGHT    MK  IDNO    CONC            NAME
1    1    4.081    57288      4928                23.2097
     2    4.492     5037       398    V            2.0406
     3    4.956    48854      3607    V           19.7924
     4    5.246   117826      8526    V           47.7356
     5    6.378     6261       512                 2.5366
     6    6.762    11564       812    V            4.6851
                  -------    ------                ------
          TOTAL   246830     18782                 100
```

METHOD FOR SEPARATING CARBOHYDRATE IN GLYCOSIDE-LINKAGE-HAVING COMPOUND, CARBOHYDRATE SEPARATING SYSTEM, CARBOHYDRATE SEPARATING REAGENT KIT, STANDARD SAMPLE FOR CARBOHYDRATE SEPARATION, AND EVALUATION SYSTEM

TECHNICAL FIELD

The present invention relates to a method for separating carbohydrate in a glycoside-linkage-having compound (for example, a glycoprotein or the like), a carbohydrate separating system thereof, a carbohydrate separating reagent kit, a standard sample for carbohydrate separation, and an evaluation system. Such a glycoside-linkage-having compound plays various and essential biological roles.

BACKGROUND ART

Glycoconjugates such as glycoproteins, proteoglycans, or glycolipids are important biological materials, which are produced by bonding protein or lipid with a carbohydrate chain that may be of various kinds. One group of the glycoconjugates, glycoproteins, is broadly classified into serotype glycoproteins and mucin glycoproteins.

In most of proteins in serum excluding albumin, carbohydrate is linked to an Asn of Asn-X-Ser/Thr residue in the proteins through N-linkage. Thus, a glycoprotein having a linkage of this type is termed as serum-type glycoprotein or N-linked glycoprotein. Further, a carbohydrate chain, which is linked to the N-linked glycoprotein, is termed as an N-linked carbohydrate chain.

On the other hand, in protein being a main component of: (i) mucus secreted from a glandular system such as a salivary gland or submandibular gland; and (ii) a mucous tissue of an inner surface of a gastrointestinal tract of a stomach, a small intestine or the like, carbohydrate is linked to Ser/Thr through O-linkage. Therefore, a glycoprotein having a linkage of this type is termed as mucin glycoprotein or O-linked glycoprotein. Further, a carbohydrate chain bonded to the O-linked glycoprotein is termed as an O-linked carbohydrate chain.

In vivo, there are various kinds of carbohydrate chains. Some proteins such as IgG, IgE, and the like, contain the N-linked carbohydrate chain. Some proteins such as submandibular gland mucin and the like contain the O-linked carbohydrate chain. Further, some proteins such as erythropoietin and the like contain both the N-linked carbohydrate chain and the O-linked carbohydrate chain.

These glycoproteins play various and essential roles in vivo. For example, a carbohydrate chain of IgG causes protein to retain its steric structure, mucin performs defense effect against xenobiotic substances, erythropoietin adjusts its metabolic rate in blood, and asialoglycoprotein has a function of being uptaken to a liver and metabolized therein. Further, it is considered that these carbohydrate chains are widely found on a surface of a cell membrane and in intercellular matrix among cells, and plays a part of essential roles in biological information network. However, details of the function of the carbohydrate chains in the biological information network have not been fully understood.

As described above, the carbohydrate chains in glycoproteins have various functions. In order to understand the functions, structural analysis should be carried out after separation of a sugar chain from a glycoprotein to which it is attached. For the structural analysis, the carbohydrate chain is cleaved from protein and then separated. With recent improvement of analyzers and methods for structural analysis, separation of a carbohydrate chain derived from glycoprotein and its structural analysis can be carried out by sophisticated separating means such as high-performance liquid chromatography and capillary electrophoresis. Further, the followings have facilitated structural analysis of a separated carbohydrate chain: (i) molecular weight measurement by a matrix-assisted laser desorption time of flight mass spectrometry or electrospray mass spectrometry; (ii) sequence determination by fragment ion analysis; and (iii) structural analysis by high-field nuclear magnetic resonance.

By fully utilizing the leading-edge analyzers described above, various methods have been realized for structural analysis, though there are still some difficulties, especially, in obtaining a required amount of carbohydrate chains separated from glycoprotein.

On the other hand, many researchers have been trying to develop a simple method for cleaving a carbohydrate chain from glycoprotein. Regardless of many studies, no simple method has been found. Therefore, in the carbohydrate chain analysis, the cleavage of the carbohydrate chain still requires experience. Further, in the analysis of a carbohydrate chain, the cleavage of the carbohydrate chain is still rate-determining step.

For example, in order to cleave an N-linked carbohydrate chain off from an N-linked glycoprotein linked to asparagine, a chemical method and an enzymatic method have been mainly used.

Specifically, hydrazinolysis has been used as a typical chemical method. In the hydrazinolysis method, a carbohydrate chain is separated by heating, at high temperature (100° C. or higher) for long hours, a solution in which a subject glycoprotein is dissolved in anhydrous hydrazine. As is generally known, however, anhydrous hydrazine is highly toxic and explosive and thus requires special care for handling. There are several methods for separating a carbohydrate chain from a glycoprotein with the use of hydrazine, and all of the methods require multiple steps: (i) pyrogenetic reaction for 3 to 24 hours; (ii) removal of hydrazine; (iii) re-acetylation of an amino group of amino carbohydrate in a carbohydrate chain; and (iv) its post-treatment. In order to complete the entire process, at least two days (48 hours) or more are required.

In the enzymatic method which is another method for separating an N-linked carbohydrate chain from an N-linked glycoprotein, a carbohydrate chain is separated by utilizing N-glycanase F found in a microorganism of flavobacterium spp. or N-glycoamidase A found in almond seeds. As a substrate, glycopeptide obtained by digestion with protease (e.g. trypsin) is often employed. Unlike the hydrazinolysis method, the enzymatic method is safe. However, the enzymatic method requires experiences due to the use of enzyme, and takes one day (24 hours) or more for achieving general enzymatic reaction. Further, as to N-glycosidase F, though recombinant products are commercially available, only a slight amount (less than milligram) is generally used due to its high price. More seriously, depending on a molecule size of enzyme as protein, some carbohydrate chains are not easily separated from glycoproteins or not separated at all. Due to such a drawback that enzymatic functions differ depending on kinds of glycoproteins, enzymatic reaction cannot be employed directly to cells and body fluids.

On the other hand, the chemical method, but not the enzymatic method, is used for separating a carbohydrate chain from an O-linked glycoprotein linked to a hydroxyl group of serine or threonine in a glycoprotein. The enzymatic method is not used, because an O-linked carbohydrate chain having eight kinds of core structures and no enzyme has been found that has a diverse spectrum that enables recognition of all of the eight kinds of core structures.

Thus, in order to separate an O-linked carbohydrate chain from an O-linked glycoprotein, an alkali decomposition method has been exclusively used. The alkali decomposition method takes an advantage of the nature of alkali, which facilitates cleaving a linkage between the O-linked carbohydrate chain and an Ser or Thr. In the alkali decomposition method, a carbohydrate chain is separated by dissolving O-linked glycoprotein in a aqueous solution at high concentration of alkali, and incubating it for long hours (generally 48 hours or longer). As to the aqueous alkali solution, sodium hydroxide of 0.1 to 0.5 M is generally used. Due to its high concentration, however, there is a fatal problem that a carbohydrate chain separated from a glycoprotein is decomposed through β-elimination reaction. The β-elimination reaction occurs due to C-1 position hemiacetal group of the carbohydrate chain cleaved from the glycoprotein.

In order to solve the problem, the alkali decomposition method is arranged such that the carbohydrate chain cleavage reaction is carried out using the alkaline solution to which a reducing agent (e.g. $NaBH_4$) is added. However, this causes its post treatment to be more complicated because the reducing terminal of the carbohydrate chain are not a hemiacetal structure and reduced to sugar alcohol, not a hemiacetal structure. As another drawback, the sugar alcohol cannot be labeled with a fluorogenic or chromogenic reagent, which is necessary for highly sensitive analysis. Therefore, the hydrazinolysis method has been used as an alternative to the alkali decomposition method. Since the hydrazinolysis method not only requires long hours for reaction and post processing, but also utilizes an highly explosive agent, the hydrazinolysis method is poor in versatility.

Recently, such methods have been reported that efficiently cleave an O-linked carbohydrate chain from O-linked glycoprotein without modifying a reducing terminal. In the methods, ammonia is used for cleaving a carbohydrate chain (Huang, Y. ; Mechref, Y. ; Novotny, M. V., 2001, Microscale nonreductive release of O-glycans for subsequent analysis through MALDI mass spectrometry and capillary electrophoresis., Anal. Chem., vol 73,6063-6069), or an O-linked glycoprotein is adsorbed in a column to separate an O-linked carbohydrate chain (Karlson, N. G.; Packer, N. H., 2002, Analysis of O-linked reducing oligosaccharides released by an in-line flow system., Anal. Biochem., vol 305,173-185).

However, the both conventional methods have to be carried out under mild condition for long hours in order to prevent a carbohydrate chain from being decomposed, because a cleaved O-linked carbohydrate chain goes through β-elimination reaction. Thus, there will be great difficulties in applying the conventional methods to clinical analysis which requires a large number of samples, or to proteome analysis or proteomics analysis which requires high throughput.

As described above, studies on the functions of carbohydrate chains have been proceeded with difficulties. One of the difficulties come from diverse structures of carbohydrate chains, in which each monosaccharide, which is component of the carbohydrate chain, has four to five hydroxyl groups respectively. However, the biggest difficulty comes from the fact that a simple method has not been found for readily cleaving a carbohydrate chain off from glycoconjugate. Specifically, as to glycoprotein, which is a conjugation of protein and a carbohydrate chain(s) with molecular weight of several ten thousands to several hundred thousands, a method for cleaving off a carbohydrate chain has been searched for thirty years. However, no excellent versatile method has been found.

Consequently, there has been a strong demand for realizing a method for separating a carbohydrate chain from glycoprotein readily and securely in a short time.

The present invention was made in view of the above problem, and an object of the present invention is to provide: (i) a method for readily separating carbohydrate in a short time by efficiently cleaving a glycoside linkage; (ii) a carbohydrate separating system for applying the method to clinical analysis or to proteome analysis or proteomics analysis which requires high throughput; (iii) a carbohydrate separating reagent kit; (iv) a standard sample for carbohydrate separation ; and (v) an evaluation method and an evaluation system for carbohydrate.

DISCLOSURE OF INVENTION

An inventor of the present invention has devoted himself for studies on cleaving a glycoside linkage in a molecule and finally found that, by applying a flow injection analysis and causing an alkaline solution to come in contact with a sample solution containing a carbohydrate-containing compound (e.g. glycoprotein) in a flow in a flow path, (i) reaction time can be dramatically shortened compared to a conventional method; and (ii) reagent to be used for the reaction can be minimized so as to be environmentally friendly.

Thus, a method for separating carbohydrate of the present invention is a separation method for separating carbohydrate, the separation method including the steps of: cleaving a glycoside linkage in a sample solution containing a glycoside-linkage-having compound; and separating carbohydrate from the sample solution, wherein the sample solution is introduced into an alkaline solution continuously passing in a flow path, and the alkaline solution and the sample solution are mixed while the alkaline solution and the sample solution are flowing in the flow path.

Thus, in the method for separating carbohydrate of the present invention, the alkaline solution and the sample solution containing the glycoside-linkage-having compound are reacted, by using a flow injection analysis (hereinafter referred as FIA method), while being passed in the flow path.

In the FIA method, a sample solution for analysis is injected into a tube having an inner diameter of 0.5 mm to 1.0 mm, and a reaction reagent is mixed into a flow of the sample solution for reaction. After the reaction takes place, subjected material is detected by absorptiometry, fluorometry or the like. The FIA method is defined in ISO or JISK0126, and currently used for mainly analyzing inorganic toxic substances contained in soil, water and sewerage, and industrial water.

Before the present invention, however, there has been no other case of applying the FIA method to a method for separating carbohydrate from a glycoside-linkage-having compound.

According to the present invention, by introducing the sample solution into the flow path, the sample solution containing the glycoside-linkage-having compound, and the alkaline solution come in contact while passing in the flow path. That is, reaction for cleaving the carbohydrate from the glycoside-linkage-having compound in the sample solution proceeds while the both solutions are passing in the flow path. This shortens reaction time for separating carbohydrate from the sample solution and realizes it in minutes. In a conventional method (enzymatic method, alkali decomposition method), reaction for separating a carbohydrate chain from glycoprotein has required days (one day or more). Thus, the method for separating carbohydrate of the present invention dramatically shortens the reaction time.

In the conventional alkali decomposition method, separated carbohydrate was sugar alcohol because decomposition of the separated carbohydrate chain was prevented with the use of a reducing agent. This has caused difficulties in isolating the sugar alcohol. According to the present invention, however, since a reducing agent is not used, the carbohydrate in the glycoside-linkage-having compound can be separated as ketose or aldose, so that the carbohydrate can be readily isolated.

According to the present invention, the application of the FIA method provides maximum effects of the FIA method: (i) simple operation; (ii) quick processing; (iii) high-precision analysis; and (iv) cost reduction.

The method for separating carbohydrate of the present invention is specifically preferable for efficiently cleaving carbohydrate and material other than carbohydrate which are in a molecule of the glycoside-linkage-having compound in a short time, so as to separate carbohydrate.

It is preferable that the glycoside-linkage-having compound be a glycoconjugate, specifically a glycoprotein. The glycoprotein is classified into an N-linked type and an O-linked type. The present invention is applicable for the both types.

The glycoconjugate such as a glycoprotein or glycolipid is biopolymer, and has various functions such as recognizing interrelation among cells, adjusting enzyme activity, and expressing hormone-like activity, etc. As to these functions, it is considered that a carbohydrate chain in glycoconjugate plays an important role. Further, a carbohydrate chain existing on a surface of a cell will be a key marker for distinguishing a healthy cell and a cancer cell because a structure of a carbohydrate chain changes as cancer transforms. Since functions of carbohydrate a chain has not been explained in many aspects, studies have been strenuously conducted for elucidating the functions by separating a carbohydrate chain from glycoconjugate. However, in the conventional method such as the enzymatic method or the alkali decomposition method, a large number of samples cannot be analyzed in a short time. This is because extremely long time (days) is required for separating a carbohydrate chain from glycoconjugate.

In the method for separating carbohydrate of the present invention, the reaction time is extremely short (in minutes), so that a large number of samples can be used. Accordingly, by separating a carbohydrate chain contained in glycoconjugate by using the method for separating carbohydrate of the present invention, analysis of structures or functions of a carbohydrate chain is dramatically speeded up. This holds significant promises for: development of a novel drug; finding of makers for various diseases; clinical analysis; or application to proteome analysis requiring high throughput.

It is preferable that after a mixed solution of the alkaline solution and the sample solution be heated to 30° C. to 150° C., the mixed solution is cooled down to below 30° C.

When the sample solution and the alkaline solution come in contact at an excessive high temperature, decomposition reaction of the separated carbohydrate is facilitated. At an excessive low temperature, cleavage of a glycoside linkage takes a long time.

According to the present invention, the decomposition reaction of the separated carbohydrate can be prevented by cooling the reaction solution down to below 30° C., after the glycoside linkage is cleaved with the alkaline solution at a temperature in a range of 30° C. to 150° C. Accordingly, the glycoside linkage contained in the sample solution is efficiently cleaved in a short time, so that the carbohydrate is separated.

In the method for separating carbohydrate of the present invention, carbohydrate is separated from the sample solution by cleaving the glycoside linkage, while the sample solution and the alkaline solution are being passed in the flow path. That is, the solution containing the separated carbohydrate contains the alkaline solution.

Thus, it is preferable that alkali be removed from the mixed solution of the sample solution and the alkaline solution. This prevents decomposition of the separated carbohydrate, so that the carbohydrate contained in the glycoside-linkage-having compound is isolated as a solution.

In the method for separating carbohydrate of the present invention, it is preferable that the separation method for separating carbohydrate include the step of: labeling the carbohydrate separated from the sample solution. That is, it is preferable to convert the separated carbohydrate into a labeled derivative.

The solution containing the separated carbohydrate generally contains at least one kind of carbohydrate, depending on a kind of glycoconjugate contained in the sample solution. Therefore, in order to determine a structure of carbohydrate, which has not been known for example, it is preferable to separate each kind of carbohydrate from a solution containing the plural kinds of separated carbohydrate (including carbohydrate chains). As described above, carbohydrate separated by using the method for separating carbohydrate of the present invention is ketose or aldose, which is capable of forming a hemiacetal structure. Thus, the separated carbohydrate can be readily reacted with a compound containing an amino group for example, and converted into a labeled carbohydrate derivative.

In this way, the labeled carbohydrate derivative can be readily detected, thereby realizing a high-sensitive analysis and supporting scale up of the sample solution. Thus, the method for separating carbohydrate of the present invention can be applied to prepare a carbohydrate chain, which has not been readily prepared using the conventional methods. As used herein, "preparing a carbohydrate chain" refers to isolating a carbohydrate chain contained in the sample solution by using a large amount of the sample solution. As described above, the method for separating carbohydrate of the present invention allows a carbohydrate chain to be efficiently prepared regardless of an amount of the sample solution, by preventing decomposition of the separated carbohydrate. That is, a carbohydrate chain can be efficiently eluted from the sample solution. This enables preparation of a carbohydrate chain related to a disease and structural analysis of the carbohydrate chain, so as to facilitate clarification of a mechanism of a disease and development of a novel drug.

A carbohydrate separating system of the present invention includes a tubule for passing a sample solution containing a glycoside-linkage-having compound and an alkaline solution; alkaline solution supplying means for continuously supplying the alkaline solution into the tubule; introducing means for introducing the sample solution in the tubule; temperature controlling means for controlling a temperature of the solution passing in the tubule; and removing means for removing alkali contained in the solution flowed out from the tubule.

The carbohydrate separating system of the present invention applies the FIA method. That is, while the alkaline solution is continuously being passed in the tubule by the alkaline solution supplying means, a certain amount of the sample solution is introduced into a flow of the alkaline solution by the sample solution introducing means provided at an appropriate portion of the tubule.

Accordingly, the sample solution is diffused while being passed in the flow of the alkaline solution in the tubule, mixed with the alkaline solution, and the reaction for cleaving a glycoside linkage proceeds. Then, the mixed solution of the sample solution and the alkaline solution, which passes in the tubule, is heated by the temperature controlling means. This facilitates the reaction for cleaving the glycoside linkage, so that the glycoside linkage can be cleaved in a short time.

Further, the tubule in the following stage of the temperature controlling means is immediately cooled down due to release from the heat of the temperature controlling means. This prevents the cleaved carbohydrate from being decomposed by alkali. The alkaline solution, which is contained in the solution containing the cleaved carbohydrate, is removed by the removing means. In this way, the carbohydrate can be prevented from being decomposed by alkali, so that the cleaved carbohydrate can be exclusively isolated as a solution containing the cleaved carbohydrate.

As described above, the carbohydrate separating system of the present invention employs an in-line system for: (i) supplying (sending) the sample solution and the alkaline solution to the tubule; (ii) introducing the sample solution to the tubule; and (iii) mixing the sample solution and the alkaline solution for reaction.

It is preferable that the carbohydrate separating system of the present invention include detecting means for detecting the carbohydrate in the solution flowed out from the tubule. According to the present invention, the carbohydrate in the solution flowed out from the tubule is detected by the detecting means provided in the preceding stage of the removing means. Accordingly, the solution containing the carbohydrate can be exclusively sent to the following removing means, so that the solution passing through the removing means can be isolated as the solution which contains the carbohydrate exclusively but the alkaline solution. In addition, this prevents the removing means from being deteriorated by the alkaline solution.

Further, it is preferable that an inner diameter of the tubule be in a range of 0.1 mm to 2 mm; and a length of the tubule to be heated by the temperature controlling means is in a range of 1 m to 20 m. This not only shortens the reaction time for cleaving the glycoside linkage, but also prevents carbohydrate from being decomposed by alkali, so that carbohydrate can be separated from the sample solution more efficiently.

A carbohydrate separating reagent kit (reagent set for separating carbohydrate) includes: a preparation reagent for preparing the sample solution; and the alkaline solution of a predetermined concentration.

With the carbohydrate separating reagent kit, the sample solution can be prepared only by adding the glycoside-linkage-having compound to the reagent kit. Thus, in the method for separating carbohydrate and carbohydrate separating system of the present invention, carbohydrate can be separated from the sample solution in a shorter time. Further, because the carbohydrate separating reagent kit includes the alkaline solution of a predetermined concentration, the method for separating carbohydrate and the carbohydrate separating system can be implemented under the same condition.

Note that, the "preparation reagent" refers to a reagent used for preparing the sample solution. The preparation reagent includes: (i) a solid or liquid reagent such as a solution for preparing the sample solution; (ii) gas to be introduced in the sample solution; and (iii) a device such as column used for preparing the sample solution from a biological sample (e.g. blood, urine, etc.).

A standard sample for use in carbohydrate separation is used for either the method for separating the carbohydrate or the carbohydrate separating system of the present invention, wherein the glycoside-linkage-having compound has a known carbohydrate.

The standard sample for carbohydrate separation includes the glycoside-linkage-having compound, which has a known carbohydrate structure. Examples of the standard sample for carbohydrate separation are: (i) glycoconjugate having a known carbohydrate structure; (ii) a carbohydrate containing compound which is chemically synthesized; or (iii) derivatives of (i) and (ii). The glycoconjugate (i) includes: glycoprotein such as bovine submandibular gland mucin, fetuin, swallow's nest, red blood cell glycophorin, etc.; and glycolipid such as glyceroglycolipid or sphingoglycolipid.

With the standard sample for carbohydrate separation, a structure of carbohydrate contained in the sample solution can be estimated, by comparing a result of separating carbohydrate from the sample solution having an unknown structure with a result of separating carbohydrate from the standard sample for carbohydrate separation.

It is preferable that the standard sample for carbohydrate separation be included in the carbohydrate separating reagent kit. With the standard sample for carbohydrate separation, comparison can be made between the result of separating carbohydrate from the sample solution having an unknown structure and the result of separating carbohydrate from the standard sample for carbohydrate separation, so that a structure of carbohydrate contained in the sample solution can be estimated with high reliability.

As described above, by applying the carbohydrate separating reagent kit and the standard sample for carbohydrate separation of the present invention to the method for separating carbohydrate or the carbohydrate separating system, operations can be continuously carried out in a short time, from separation of carbohydrate in the sample solution to structural analysis of the carbohydrate.

For a fuller understanding of the nature and advantages of the invention, reference should be made to the ensuing detailed description taken in conjunction with the accompanying drawings.

BRIEF DESCRIPTION OF DRAWINGS

FIG. 7 is a view showing carbohydrate chains which are mainly contained in the bovine submandibular gland mucin, and results of the MALDI-TOF MS shown in FIG. 6.

Note that, numerical references used in figures indicate as follows: A: in-flow chemical reaction system (carbohydrate separating system); 1: alkaline solution; 2: an inert gas cylinder; 3: a pump (alkaline solution supplying means); 4: a sample injection device (sample introducing means); 5: a mixing unit; 6: a thermostat bath (temperature controlling means); 7: a reaction tube (tubule or flow path); 8: a detector (detecting means); 9: recording sections; 10a and 10b: switching valves; 11a and 11b: a waste section; 12: an ion-exchange column (removing means); 13: a sample tube; 14: a carbohydrate chain (carbohydrate).

BEST MODE FOR CARRYING-OUT THE INVENTION

Figure 1:
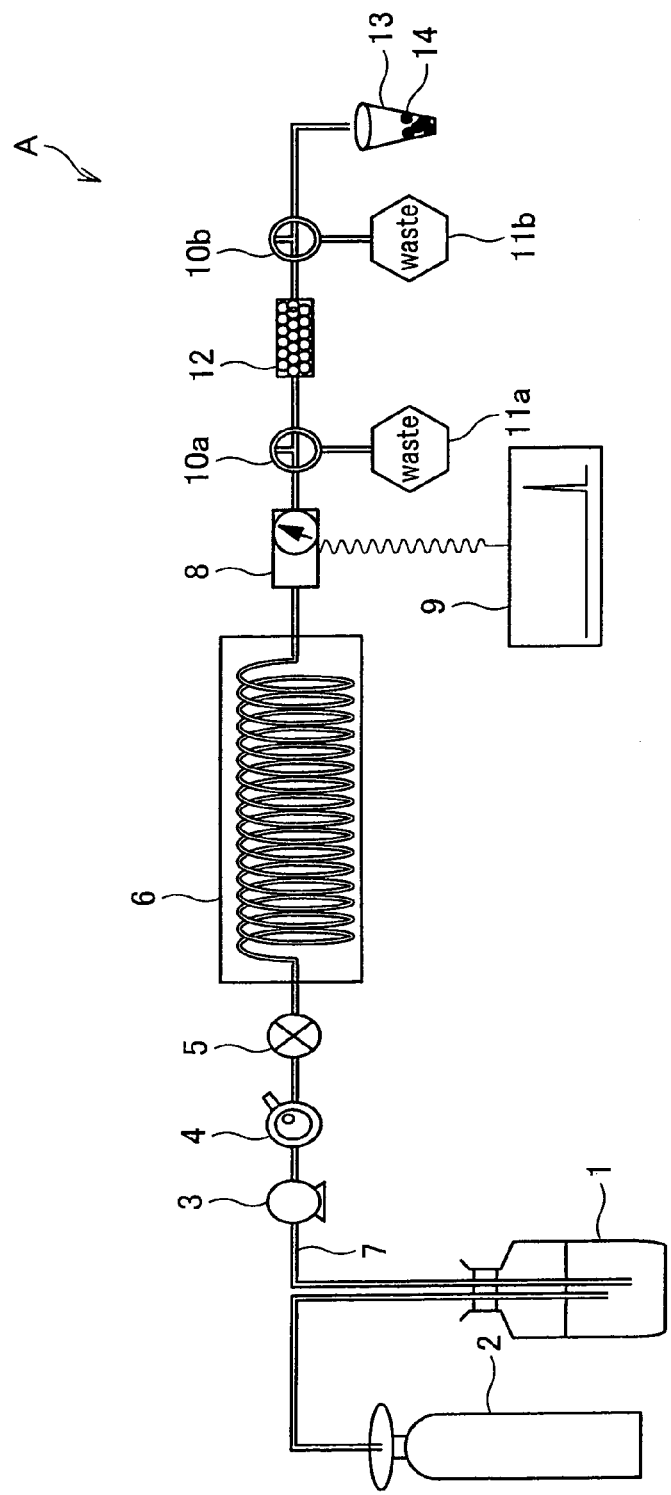
FIG. 1 is a block diagram schematically illustrating a structure of an in-flow chemical reaction system of the present invention.
Figure 2:
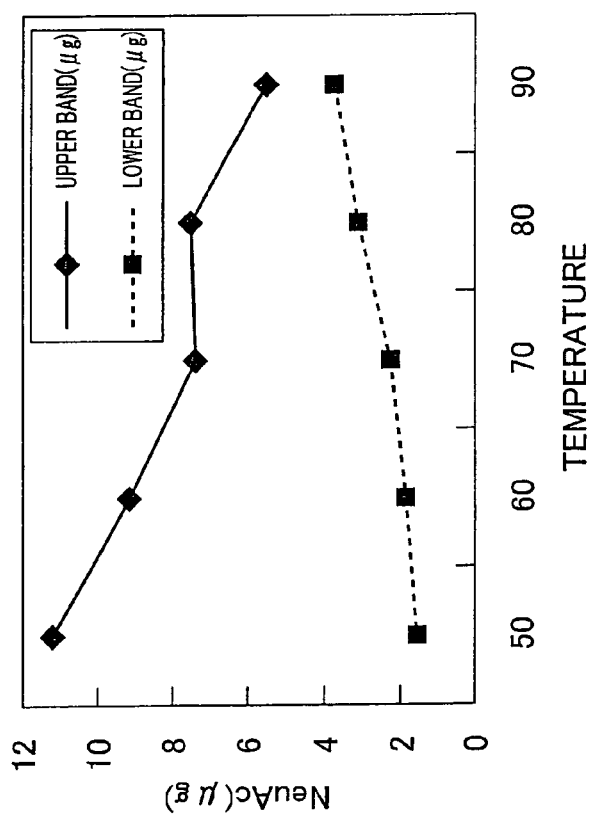
FIG. 2($a$) and FIG. 2($b$) are views showing results of separating a carbohydrate chain from bovine submandibular gland mucin at various temperatures and with various lengths of the reaction tube inside a thermostat bath. Here, the length of the reaction tube was 1.5 m.
Figure 3:
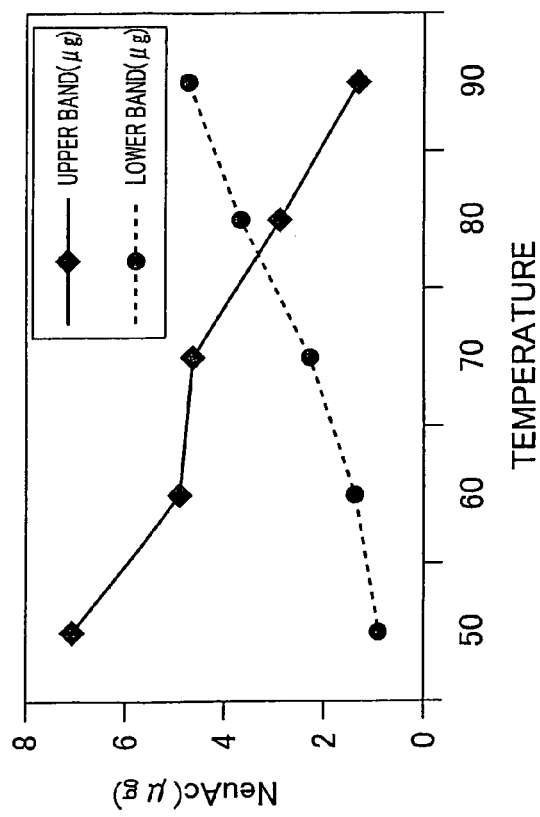
FIG. 3($a$) and FIG. 3($b$) are views showing results of separating the carbohydrate chain from bovine submandibular gland mucin at various temperatures and with various lengths of the reaction tube inside the thermostat bath. Here, the length of the reaction tube was 3 m.

With reference to FIG. 1, one embodiment of the present invention is described below. Note that, the present invention is not limited to this.

A method for separating a carbohydrate chain from glycoprotein of the present invention separates carbohydrate from a sample solution which contains a glycoside-linkage-having compound, by (i) causing the sample solution come in contact with alkaline solution in a flow path, and (ii) resolving a glycoside linkage in the glycoside-linkage-having compound.

As used herein, the "glycoside-linkage-having compound" refers to a compound having a portion of a glycoside linkage to carbohydrate in a molecule. Examples of the glycoside-linkage-having compound are glycoconjugates in which peptide, protein, lipid, or a base is bonded to a carbohydrate. That is, the examples of glycoconjugates include glycoproteins, glycolipids, and nucleic acid. The carbohydrate in the glycoside-linkage-having compound may be monosaccharide, or a carbohydrate chain-forming saccharide carbohydrate such as olligosaccharide or polysaccharide.

The glycoside linkage is formed, for example, through dehydration condensation between a reducing terminal of carbohydrate (i.e. anomeric hydroxyl group) and a functional group of carbohydrate or a functional group of other compound such as a hydroxyl group (—OH), an amino group (—NH$_2$), or a thiol group (—SH). The, hydroxyl group, the amino group, or the thiol group may be a functional group which can form acetal with aldose or ketose. In other words, the glycoside-linkage-having compound may be a compound which has one or more O-glycoside linkages, N-glycoside linkages, or S-glycoside linkages.

In the following examples, a method for separating a carbohydrate chain contained in a glycoprotein, which is a glycoside-linkage-having compound, is described.

First, the following describes a principle of a method for: separating a carbohydrate chain in the glycoprotain according to the present invention.

Conventionally, alkali decomposition has been predominantly used for separating a carbohydrate chain from glycoprotein. However, in the alkali decomposition method, since a separated carbohydrate chain is further decomposed by alkali, reaction must have been carried out under mild condition in order to prevent the further decomposition reaction as much as possible.

In the method for separating a carbohydrate chain by the alkali decomposition, reaction proceeds in two stages as shown in (1) and (2) below.

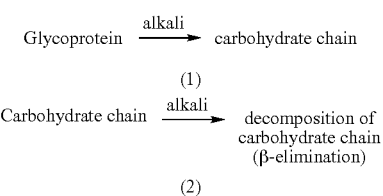

In the conventional alkali decomposition method, the decomposition reaction takes place in the presence of a reducing agent in order to suppress the decomposition reaction of a carbohydrate chain (e.g. β-elimination), which is expressed in the Formula (2). As a result, a reducing terminal of the carbohydrate chain is also reduced by the reducing agent, so that a resulting carbohydrate chain will be sugar alcohol. Specifically, the resulting carbohydrate chain will be sugar alcohol reduced from a carbonyl group of aldose or ketose. Since the resulting carbohydrate chain will be linear sugar alcohol which cannot form a hemiacetal structure, post process will be very complex in the alkali decomposition method.

In the view of the above problem, the present inventor has invented an in-flow chemical reaction system that can efficiently separate a carbohydrate chain by: (i) carrying out an cleavage reaction of a glycoside linkage; and (ii) separating the carbohydrate chain cleaved in the Formula (1) from a reaction system before decomposition reaction expressed in the Formula (2) starts.

In the in-flow chemical reaction system, reaction expressed in the Formula (1) is carried out rapidly at a high temperature, and a carbohydrate chain is separated from the reaction system before the reaction expressed in the Formula (2) starts. This significantly shortens reaction time.

FIG. 1 is a view schematically illustrating a structure of the in-flow chemical reaction system (a carbohydrate chain separating device and carbohydrate separating system). The system basically includes a pump (alkaline solution supplying means) 3 for continuously sending a liquid to a reaction tube 7, a sample injection unit (sample solution introducing means) 4, a thermostat bath (temperature controlling means) 6, the reaction tube (tubule or flow path) 7, a detector 8, switching valves 10a and 10b, and an ion-exchange column (removing means).

The alkaline solution 1 is filled with an inert gas such as nitrogen or argon, which are supplied from an inert gas cylinder 2, and controlled to flow in the system at a certain flow rate by the pump 3.

In the following stage of the pump 3, the sample injection unit 4 is provided. From the sample injection unit 4, a sample solution containing glycoprotein is introduced to the alkaline solution that continuously flows in the reaction tube 7 at the certain flow rate. When the sample solution is injected from the sample injection unit 4, a mixing unit 5 mixes the sample solution and the alkaline solution for a predetermined period of time. The mixed solution is finally supplied to the thermostat bath 6 and then retained at a certain temperature in the thermostat bath 6. In the thermostat bath 6, cleavage reaction of the carbohydrate chain from the glycoprotein takes place. That is, glycoside linkage in the glycoprotein is cleaved and the carbohydrate chain is separated, while the mixed solution passes in the reaction tube 7 in the thermostat bath 6.

Though a reaction rate of cleaving glycoside linkage varies depending on a kind of glycoproteins, the reaction rate is extremely low when the thermostat bath 6 is not heated. Thus, most carbohydrate chains are conceivably not to be separated.

After the mixed solution passes through the thermostat bath 6, a temperature in the reaction tube 7 is returned to room temperature due to release from the heat of the thermostat bath 6, so that the mixed solution in the reaction tube 7 is immediately cooled down. Accordingly, in the reaction tube 7 in the subsequent stage of the thermostat bath 6, a reaction rate for cleaving glycoside linkage become negligibly low. In addition, the β-elimination reaction of the separated carbohydrate chain can be mostly ignored, because reaction time in the thermostat bath 6 is extremely short.

As described above, the in-flow chemical reaction system A enables the reaction of the Formula (1) alone to be proceeded, by applying heat to the sample solution and the alkaline solution in the thermostat bath 6 for a short time. Compared to the conventional methods, this significantly reduces time for separating a carbohydrate chain and realizes it in minutes.

In the in-flow chemical reaction system A, a time for eluting a sample solution from the thermostat bath 6 is calculated easily. The sample solution has been introduced by the sample injection unit 4. Further, the mixed solution, which has passed through the thermostat 6 and then eluted from the reaction tube 7, is monitored by the detector 8. While the separated carbohydrate chain is eluted, the valve 10a is switched from the waste (waste section) 11a side to the ion-exchange column 12 side. In this manner, only the mixed solution containing the carbohydrate chain is passed to the ion-exchange column 12 which is filled with a positive ion exchange resin. This enables removal of alkali from the mixed solution containing carbohydrate chains, thereby collecting a carbohydrate chain 14 into a sample tube 13. When another detector 8 is provided between the ion-exchange column 12 and the valve 10b, it becomes possible to switch the valve 10b monitoring the solution with the detector 8. This makes it possible to certainly collect, in the sample tube 13, the solution containing the carbohydrate chain 14.

Here, assume reaction for separating carbohydrate, which requires 48 hours at 30° C. and doubles its reaction rate for every 10° C. When the reaction takes place in the in-flow chemical reaction system A at 90° C., its reaction rate will be conceivably multiplied exponentially with temperature. Thus, a reaction rate at 90° C. will be 64 times of a reaction rate at 30° C.

As described in an example below, when an in-flow chemical reaction system A including the reaction tube 7 having a length of 10 m is used for separating a carbohydrate chain from bovine submandibular gland mucin, it becomes possible to efficiently cleave off an O-linked carbohydrate chain. In the example, separation of a carbohydrate chain is completed within three minutes (180 seconds) as a solution passes through the thermostat bath 6. This means, the present invention reduces reaction time down to one thousandth of the reaction time required for the conventional alkali decomposition reaction (i.e. 48 hours). After the mixed solution is eluted from the reaction tube 7 in the thermostat bath 6, which is thermostated at 90° C., a reaction temperature immediately returns to room temperature because the reaction tube is extremely thin (internal diameter: 0.3 mm). Further, by passing the mixed solution through the ion-exchange column 12 (capacity: 1 mL), and thereby removing the alkaline solution (desalting), the O-linked carbohydrate chain 14 can be efficiently collected in the sample tube 13.

For example, a reaction rate for cleaving a glycoside linkage between carbohydrate and carbohydrate in the glycoprotein is much slower than that for cleaving a glycoside linkage between protein and carbohydrate in the glycoprotein, so that carbohydrate of the carbohydrate chain 14 to be collected into the sample tube 13 will not be cleaved. That is, a carbohydrate structure of the carbohydrate chain contained in the sample solution is preserved. Thus, a carbohydrate chain is separated from the sample solution containing the glycoprotein in a short time, thereby collecting the separated carbohydrate chain.

As described above, in the in-flow chemical reaction system A, the sample solution containing a glycoprotein is added into the reaction tube 7, in which the alkaline solution 1 continuously flows at a certain flow rate. As a result, a carbohydrate chain in the glycoprotein is cleaved off in the reaction tube 7 in the thermostat 6, where a constant temperature is maintained. The mixed solution of the sample solution and the alkaline solution 1 is eluted from the thermostat bath 6 in a short time (normally within three minutes). Therefore, it is possible to remove alkali from the eluate by passing the eluate through the ion-exchange column 12. That is, the ion-exchange column 12 may be referred to as a post-processing unit after a carbohydrate chain is separated from the sample solution.

Thus, the in-flow chemical reaction system A is extremely useful for efficiently separating carbohydrate from the sample solution in a short time. The in-flow chemical reaction system A can be also used as a carbohydrate chain auto sequencer, which determines primary sequence of a known or unknown carbohydrate chain.

Further, the in-flow chemical reaction system A carries out all the operations in an in-line reaction system, thereby eliminating post processing for naturalization or desalting, which is required for the conventional methods. In addition, the in-flow chemical reaction system A realizes high throughput without difficulty by using an auto sampler and a fraction collector.

Unlike the conventional methods, a reducing agent is not used, so that the carbohydrate chain 14 collected into the sample tube will be aldose or ketose, which can form a hemiacetal structure. Accordingly, the separated carbohydrate chain 14 can be easily labeled and converted into a carbohydrate derivative. Therefore, the separated carbohydrate chain 14 can be used in high-sensitive analysis. Thus, even when multiple kinds of carbohydrate derivatives are contained in the sample tube 13, the carbohydrate derivatives can be separated, for example, by HPLC. With highly developed techniques such as mass spectrometry, NMR, HPLC, etc., a carbohydrate chain can be analyzed, thereby realizing a structural analysis of a carbohydrate chain (such as. determination of primary sequence of a carbohydrate chain).

A method for labeling is not specifically limited. For example, fluorescent material, enzyme-related material, radioactive isotope, light emitting material, ultraviolet absorption material, spin labeling agent, or the like may be bonded to carbohydrate. With these, labeled carbohydrate can be separated from a solution containing separated carbohydrate, even when the solution contains impurities or multiple kinds of carbohydrates.

As reagent for labeling, a compound containing an amino group, for example, an aminobenzene derivative (e.g. 3-aminobenzoic acid), a 2-aminobenzene derivative, an aminonaphthalene derivative, or APTS (9-aminopyrene-1,4,6 trisulfonate) may be used. With these, a carbohydrate derivative can be detected with high sensitivity, thereby making it possible to separate a labeled carbohydrate derivative from the solution containing separated carbohydrate.

Further, if a standard data is created based on data of individual carbohydrates obtained by labeling and separation, a carbohydrate structure contained in a sample solution can be estimated by comparing the standard data with data of the sample solution containing separated carbohydrate, even when the carbohydrate in the sample solution is not known. For example, by creating a standard data of a labeled carbohydrate derivative separated by HPLC, a structure of carbohydrate can be estimated based on retention time for a sample solution in which carbohydrate is separated under the same condition. Further, structural analysis of carbohydrate (labeled carbohydrate derivative) can be carried out in combination of (i) mass spectrometry, NMR analysis, or the like, and (ii) HPLC.

Note that, in the in-flow chemical reaction system A illustrated in FIG. 1, the following modification may be made, for example.

As an alkaline solution, inorganic alkali or organic alkali may be used. Inorganic alkali may be alkali metal hydroxide or alkali earth metal hydroxide: (e.g. sodium hydroxide, potassium hydroxide, lithium hydroxide, or barium hydroxide), and organic alkali may be a nitrogen-containing compound such as ammonia or triethylamine.

With a low-concentration alkaline solution, a reaction rate for separating a carbohydrate chain from glycoporotein is decelerated, so that the reaction takes long time. On the other hand, with a low concentration alkaline solution, a reaction rate for decomposing a separated carbohydrate chain is accelerated, so that decomposition of a carbohydrate chain is facilitated. Thus, it is preferable that a concentration of alkaline solution be 0.05 to 2.0 M. It is more preferable that a concentration of alkaline solution be 0.1 to 0.5M. This realizes cleavage of a carbohydrate chain from a glycoprotein in a short time, while preventing decomposition of the cleaved carbohydrate chain.

The reaction tube 7 is provided in a spiral fashion so as to effectively utilize a space in the thermostat bath 6. However, the shape of the reaction tube 7 is not limited to this.

Further, a flow rate of the pump 3 is not specifically limited, and may be adjusted according to a length or a diameter of the reaction tube 7. Normally, it is preferable that the flow rate be 0.05 mL to 5 mL. It is more preferable that the flow rate be 0.1 mL to 1.0 mL. This enables the samples, i.e., the glycoprotein and the alkaline solution, to be introduced into the reaction tube 7 at a certain flow rate, so that a carbohydrate chain can be separated.

When a temperature in the thermostat bath 6 is too low, a reaction rate for separating a carbohydrate chain from a glycoporotein is decelerated, so that the reaction takes long time. On the other hand, when a temperature in the thermostat bath 6 is too high, a reaction rate for decomposing the separated carbohydrate chain is accelerated, so that decomposition of the carbohydrate chain is facilitated. Thus, a temperature in the thermostat bath 6 may be maintained in a range from room temperature to 150° C., preferably from 30° C. to 100° C., or more preferably from 70° C. to 90° C. This realizes cleavage of a carbohydrate chain from a glycoprotein in a short time while preventing the cleaved carbohydrate chain from being decomposed.

When the reaction tube 7 has a too large inner diameter, a temperature of the mixed solution, which contains the glycoprotein and the alkaline solution and flows in the reaction tube 7, cannot be stable due to heat applied to the thermostat bath 6. In addition, the mixed solution discharged from the thermostat bath 6 cannot be cooled down immediately. As a result, reaction for separating a carbohydrate chain may be decelerated or reaction for decomposing a carbohydrate chain may be accelerated. Thus, it is preferable that an inner diameter of the reaction tube 7 be small. Specifically, it is preferable that the inner diameter be 0.05 mm to 2 mm. It is more preferable that the inner diameter be 0.1 mm to 0.5 mm. This regulates heating and cooling the mixed solution, thereby efficiently proceeding separation reaction of a carbohydrate chain while preventing decomposition of the separated carbohydrate chain.

Further, when the reaction tube 7 is too long, heating the thermostat bath 6 takes long time, so that separation reaction of a carbohydrate chain ends and decomposition reaction of the carbohydrate chain is carried on within the reaction tube 7. When the reaction tube 7 is too short; separation reaction of a carbohydrate chain is not completed, so that non-reacted glycoprotein remains. Thus, even though there is no particular limit in the length of the reaction tube 7 in the thermostat bath 6, it is preferable that the length of the reaction tube 7 in the thermostat bath 6 be 1 to 20 m. It is more preferable that the length of the reaction tube 7 in the thermostat bath 6 be 3 to 10 m. This enables separation reaction of a carbohydrate chain to be efficiently proceeded while preventing decomposition of the separated carbohydrate.

As to material of the reaction tube 7, there is no restriction and any material may be used which exhibits stability against an alkaline solution, such as Teflon® for example.

In the in-flow chemical reaction system A illustrated in FIG. 1, the glycoprotein solution and the alkaline solution are mixed by the mixing unit 5 for a certain period of time. Then, the mixed solution is introduced into the reaction tube 7 in the thermostat bath 6. However, by mixing the sample solution and the alkaline solution previously, a mixed solution may be introduced from the sample injection unit 4. In this case, the mixing unit 5 is not necessary.

By using an ion dialysis membrane, ion exchange membrane, or electric desalting unit in lieu of the ion-exchange column 12, a scale-up is readily realized and a carbohydrate chain can be collected in a shorter time. Further, by providing a fraction collector in the following stage of the ion-exchange column 12, a carbohydrate separating system can be fully automated.

Here, an antibody column, in which an antibody specific to a certain carbohydrate chain as an antigen is fixed, may be disposed in an upstream or downstream of the ion-exchange column 12, so that the solution discharged from the tubule flows through the antibody column. With this arrangement, it is possible to determine whether the carbohydrate chain being the antigen of the antibody is contained in the sample solution. That is, the presence of a carbohydrate chain antigen in the sample solution can be detected. Further, an antigen bonded to the antibody can be isolated by cleaning the antibody column and cleaving an antigen-antibody combination.

The above description is made as to the method for cleaving a carbohydrate chain from glycoprotein. However, carbohydrate (carbohydrate chain) can be separated from any kind of carbohydrate-containing compound having a glycoside linkage in its molecule.

As described above, the in-flow chemical reaction system A dramatically speeds up separating a carbohydrate chain from the sample solution containing a glycoprotain, thereby achieving remarkable reaction efficiency. More specifically, the in-flow chemical reaction system A cuts reaction time for cleaving a carbohydrate chain down to three minutes or shorter. In the conventional methods, one day or more has been required for the cleavage reaction. That is, operations for achieving the reaction is simplified by 500 times or greater. Further, a reducing agent is not used in the present invention. This allows a reducing terminal to be readily labeled and converted to a carbohydrate derivative. Thus, the present invention is applicable to high-sensitive analysis. In addition, the carbohydrate derivative may be used for drug material.

Further, a carbohydrate separating reagent kit is preferably provided at least with a reagent for preparing a sample solution, and an alkaline solution having a predetermined concentration.

Thus, the sample solution can be prepared only by adding a glycoside-linkage-having-compound to the reagent kit. In addition, the -in-flow chemical reaction system A can be constantly implemented under the same condition. Note that, the carbohydrate separating reagent kit may include various reagents for better detection sensitivity or for facilitating the separation of the carbohydrate.

Further, it is preferable that a glycoside-linkage-having compound having a known carbohydrate structure be used for a standard sample for use in the carbohydrate separation. For example, bovine submandibular gland mucin described in the following example may be used.

Thus, a carbohydrate structure contained in a sample solution can be estimated by comparing sets of spectrum data: (i) a result obtained from separating carbohydrate from a sample solution having an unknown carbohydrate structure; and (ii) a result obtained from separating carbohydrate from the standard sample for carbohydrate separation.

It is more preferable that the standard sample for use in carbohydrate separation be included in the carbohydrate separating reagent kit. This provides high reliability in estimating a carbohydrate structure contained in a sample solution, because comparison can be made under the same condition between (i) the result of separating carbohydrate from a sample solution having an unknown carbohydrate structure and (ii) the result of separating carbohydrate from the standard sample for carbohydrate separation.

As described above, by applying the carbohydrate separating reagent kit and the standard sample for use in carbohydrate separation of the present invention to a method for separating carbohydrate or a carbohydrate separating system, operations can be continuously carried out in a short time, from separation of carbohydrate in a sample solution to the structural analysis of the carbohydrate.

The carbohydrate separating system (the present system) and the method for separating carbohydrate of the present invention have the following advantages, and thus highly useful significantly.

The present system significantly shortens time for separating a carbohydrate chain from a glycoprotein, which has conventionally required long hours (days). That is, the separation of a carbohydrate chain from a glycoprotein, which has conventionally required one day or more, can be carried out in minutes.

As to functions of glycoconjugate, studies are conducted as national projects and keenly competed especially among the United States, European countries, and Japan. Functional analysis of glycoconjugate mainly requires (i) purification (isolation) of glycoconjugate, (ii) cleavage of a carbohydrate chain from the glycoconjugate, and (iii) analysis of a carbohydrate chain. Specifically, techniques for cleaving a carbohydrate chain are still under development, and analysis of glycoconjugate is rate determining step. Since the present system allows a carbohydrate chain to be cleaved in a remarkably shorter time (500 times shorter) than conventional methods, extremely high usability is achieved.

The present system employs the in-line reaction device, where, while an alkaline solution (reaction reagent) is sent with a pump, a sample solution containing glycoconjugate is injected, thereby cleaving a carbohydrate chain from the sample solution. Thus, the present system is different from the conventional methods, which cause a sample containing glycoconjugate and the like to be adsorbed in a column, and then flows an alkaline solution through the column thereby to cause the reaction.

The present system facilitates qualitative evaluation of a glycoprotein-based compound (e.g. glycoprotein-based drug). Further, the present system contributes to development of a glycoprotein-related drug, quality evaluation of a carbohydrate-chain-related compound and application of a carbohydrate-chain-related compound to clinical examination, development of the carbohydrate-chain-related novel drug, etc. In other words, the present system or method for separating carbohydrate is an evaluation system or method for evaluating a sample. As used herein, what is meant by the term "evaluating a sample" is, for example: (i) identification (estimation) of a kind or amount of carbohydrate contained in the sample based on a result of separating a carbohydrate chain in the sample; (ii) identification (estimation) of a derived cell of a sample, (iii) estimation of a carbohydrate chain involved in a disease by comparing carbohydrate chains contained in healthy cells and diseased cells; and (iv) clinical examination, (v) or the like. That is, the evaluation system or the evaluation method enables: (i) qualitative evaluation of carbohydrate or a sample; (ii) evaluation of a difference in a content ratio of carbohydrate chains between healthy cells and diseased cells; and (iii) evaluation as to whether or not a disease is onset, for example. Accordingly, from a difference in the content ratio of carbohydrate chains, a relation between the carbohydrate chains and a disease can be understood, and the understanding of the relation can be used to elucidate a pathological mechanism, development of a novel drug, and clinical examination. Further, the evaluation system or the evaluation method can be applied to clinical analysis on tracing a change of a carbohydrate chain of glycoconjugate in a biological sample such as a serum or tissue extract.

In the evaluation system (or evaluation method), it is preferable that a sample be evaluated based on a content ratio of kinds of carbohydrate contained in the sample. As shown in the following examples, because kinds of carbohydrate chains contained in a sample solution may be substantially the same, evaluation of the sample (identification for the sample) may be difficult solely based on the kinds of carbohydrate. In this case, the sample can be evaluated based on the content ratio of the carbohydrates contained in the sample (ratio of plural kinds of carbohydrates). With this, high reliability is achieved in evaluation.

When the present system is used as a carbohydrate evaluation system, evaluation can be carried out in a short time by using the reagent kit and the standard sample.

Further, the present system can be applied to a method for manufacturing material of a novel carbohydrate-chain-containing drug, by rapidly preparing a carbohydrate chain, which is difficult to be synthesized, from an animal sample.

In the present system, a carbohydrate chain can be separated from not only O-linked glycoprotein but also N-linked glycoprotein. Thus, any kind of analysis of a carbohydrate chain can be carried out in a single device, so that the present system may be available in place of a conventional system.

In the present system, a use of a reagent can be reduced by a great amount by separating a carbohydrate chain in the flow injection system and thereby achieving reaction in a short time. That is, the present invention provides an extremely useful system, which realizes cost reduction for a reagent to be used, and which is environmentally friendly.

Further, the present system offers prospects of exploiting a novel field in an industry related to pathology examination and clinical examination based on abnormality of a carbohydrate chain. Further, the present system significantly simplifies analysis of a carbohydrate chain, which have been difficult to be applied to general analysis. New potentials are opened for a novel field of clinical chemistry, by analyzing a carbohydrate chain in blood or urine, or by tracing changes of a carbohydrate chain in cancer cells or inflamed issues, for example, which are accompanied by qualitative and quantitative changes of glycosyltaransferase in cancer, inflammation, or the like.

Further, the present system is expected to be applicable to development of a novel drug, by tracing changes of the carbohydrate chains and thereby: regulating glycosyltransferase or carbohydrate hydrolytic enzyme which is related to carbohydrate-chain synthesis; or controlling protein (receptor) which recognizes a carbohydrate chain.

Further, when a structure of a carbohydrate chain having a novel function is identified with the present system, an antibody against the carbohydrate chain may highly possibly be useful for an antibody drug, or detection and screening of the carbohydrate chain.

As to variations in glycosyltransferase or carbohydrate hydrolytic enzyme, genetic causes cannot be denied. Recently, studies on a congenital metabolic disorder related to a carbohydrate chain have been strenuously conducted in Europe and the United States. The present invention holds promises of greatly promoting these studies including researches on prenatal diagnosis. Such contribution is significant in regard to mankind's well-being and welfare.

Further, with the use of the in-flow chemical reaction system, the present system readily realizes a scale-up by providing an appropriate ion dialysis membrane, ion exchange membrane, or electric desalting unit, in the following stage of the thermostat bath. This enables preparation of a large amount of carbohydrate chains derived from glycoprotein by (i) using an easily accessible protein (e.g. ovalbumin, vitellus IgY, bovine submandibular mucin, porcine gastric mucosa, etc.) as material; and (ii) continuously carrying out reaction for cleaving a carbohydrate chain in the in-flow chemical reaction system A. The obtained carbohydrate chains are expected as materials for achieving high functionality of protein-based drugs.

The present invention is not limited to the above embodiment, and modifications are intended to be included within scope of the following claims.

EXAMPLE 1

Separation of Carbohydrate Chain of Bovine Submandibular Gland Mucin

Bovine submandibular gland mucin is a typical mucin protein, which is commercially available as biochemical reagent. Bovine submandibular gland mucin contains various kinds of carbohydrate chains shown in FIG. 7. With a solution (10 μL) of bovine submandibular gland mucin (0.1 mg), alkali decomposition was carried out by means of the in-flow chemical reaction system illustrated in FIG. 1. In the system, a flow rate was 0.5 ml/min and an alkaline solution was a 0.5 M lithium hydroxide solution. By using sialic acid as an indicator, efficiency of the in-flow chemical reaction system (lengths of the reaction tube, reaction temperatures) in terms of the alkali decomposition was tested. Sialic acid was present in a filtrate (low molecular side, including oligosaccharide) obtained through an ultrafiltration membrane. The ultrafiltration membrane cut off a reaction solution with molecule weight of 10000, which was collected through a small column filled with an ion-exchange resin. Results of the tests are illustrated in FIGS. 2(a) through 5(b). In FIGS. 2(a) through 5(b), filtrates obtained through the ultrafiltration membrane is lower band, and washings obtained from washing the ultrafiltration membrane (i.e., reaction solution of materials that did not pass the ultrafiltration film) is upper band. Based on the results of measuring fluorescence of each. band, carbohydrate chain content in each band is calculated.

Figure 4:
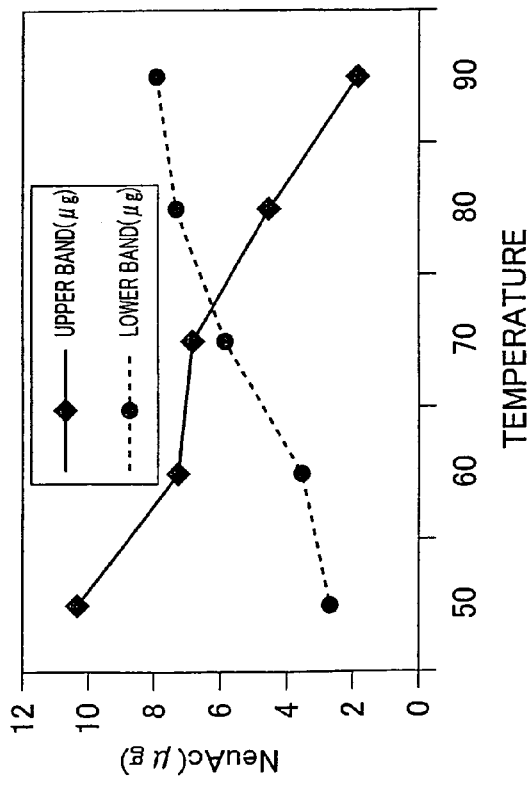
FIG. 4($a$) and FIG. 4($b$) are views showing results of separating the carbohydrate chain from bovine submandibular gland mucin at various temperatures and with various lengths of the reaction tube inside the thermostat bath. Here, the length of the reaction tube was 5 m.
Figure 5:
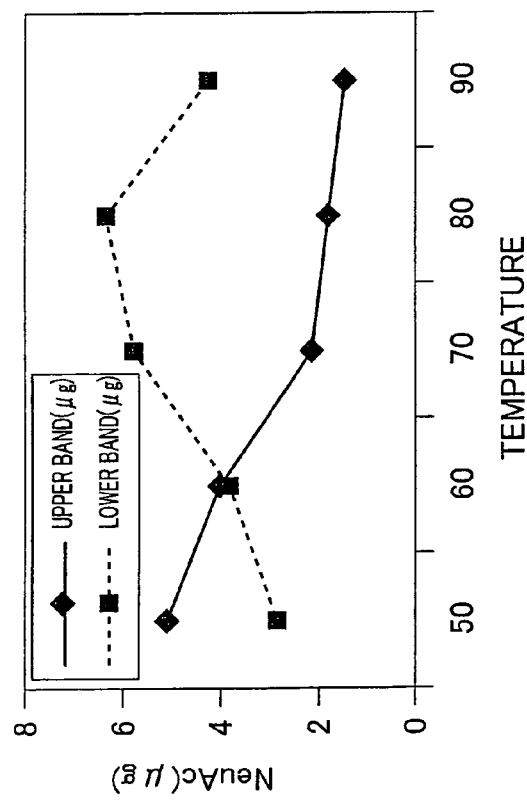
FIG. 5($a$) and FIG. 5($b$) are views showing results of separating the carbohydrate chain from bovine submandibular gland mucin at various temperatures and with various lengths of the reaction tube inside the thermostat bath. Here, the length of the reaction tube was 10 m.

As shown in FIGS. 4 and 5, a carbohydrate chain can be separated from mucin most efficiently with the reaction tube of 5 m at a reaction temperature of 90° C., or with a reaction tube of 10 m at a reaction temperature of 80° C.

Figure 6:
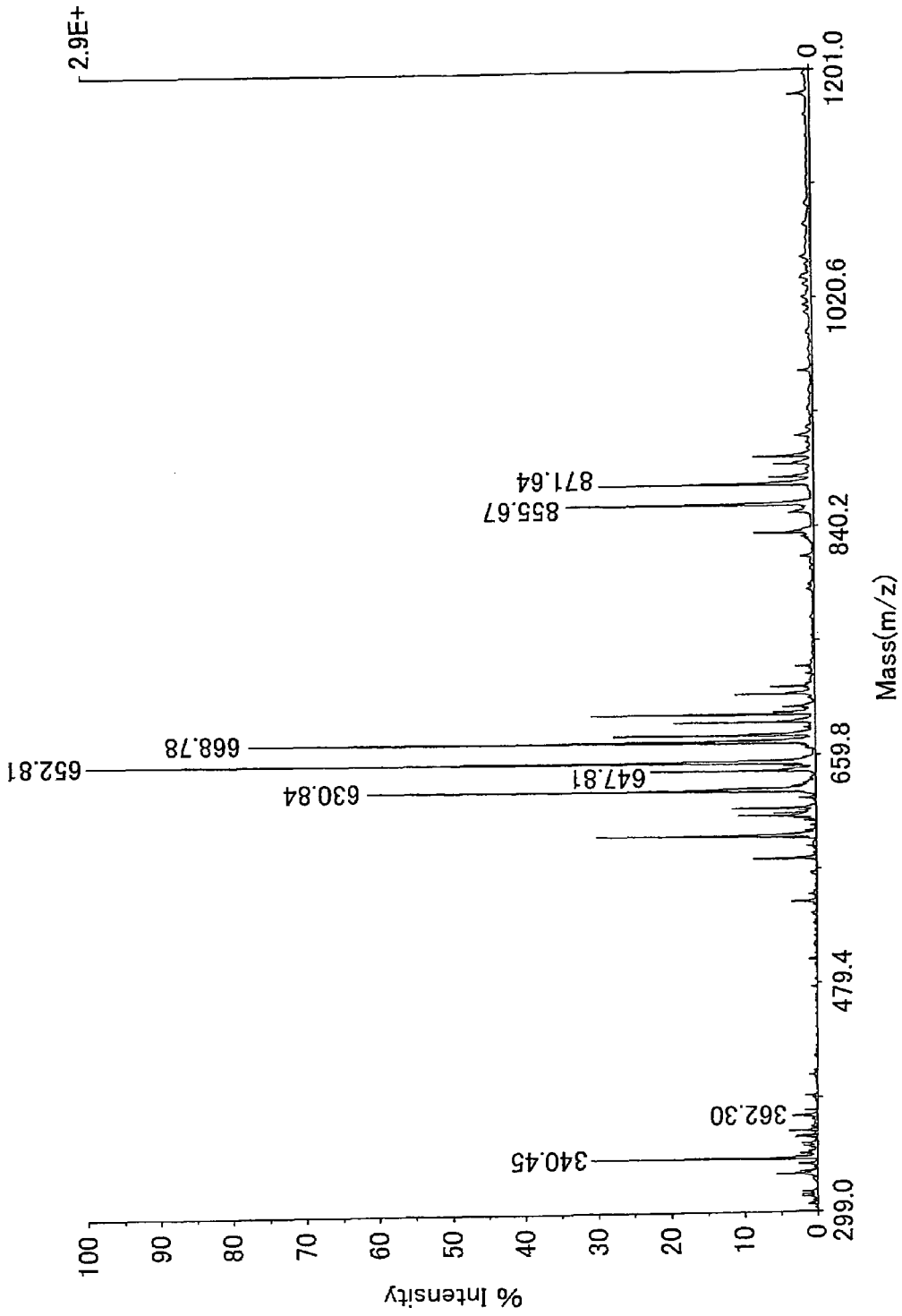
FIG. 6 illustrates mass spectrum of a carbohydrate chain separated from the bovine submandibular gland mucin by means of the in-flow chemical reaction system shown in FIG. 1, the spectrum being obtained by MALDI-TOF MS.

After drying the collected solution under reduced pressure, compounds obtained from the drying were labeled as 3-aminobenzoic acid derivatives, and analyzed by HPLC and a matrix-assisted laser desorption ion time of flight mass spectrometry (MALDI-TOF MS). The results of the MALDI-TOF MS are shown in FIG. 6. FIG. 7 is a list of typical 3-aminobenzoic acid derivatives (3-AB in FIG. 7) of oligosaccharide found in submandibular gland, and their (i) theoretical molecular weights (molecular weights indicated below structural formulas), (ii) estimated molecular ions ([M+H]+), and (iii) sodium-added molecular ions ([M+Na]+) are presented. By MALDI-TOF MS, as shown in FIG. 7, the expected ions were clearly observed in a carbohydrate-chain mixture obtained by the in-flow chemical reaction system (indicated in "flow system A" column). The "standard" column in FIG. 7 presents molecular weight of carbohydrate chains separated by using a conventional method.

Figure 8:
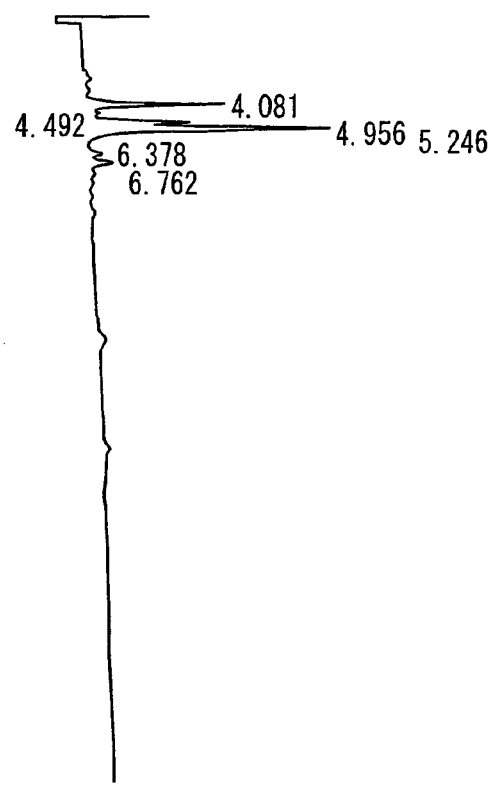
FIG. 8 is a view showing a result of HPLC analysis of carbohydrate chains, which were separated from the bovine submandibular gland mucin, by means of the in-flow chemical reaction system shown in FIG. 1.

FIG. 8 shows results of analyzing the 3-aminobenzoic acid derivatives of carbohydrate chains by HPLC. As shown in FIG. 8, it was proved that carbohydrate was efficiently cleaved from mucin glycoprotein, carbohydrate chain derivatives labeled could be prepared using reducing terminals of the carbohydrate chains thus cleaved therefrom, and further the derivatives could be separated. That is, the results prove that carbohydrate chains obtained in the example still retain a hemiacetal structure. Note that, HPLC an analysis was carried out under the following conditions: column: ODS (4.6 mm×150 mm); eluete: a linear gradient elution (2% :to 18%) with 0.1 M ammonium acetate buffer of acetonitrile (pH 6.0)); flow late: 1 ml/min; detection: fluorescence detection (excitation wavelength 305 nm, fluorescence wavelength 405 nm).

EXAMPLE 2

Separation of Carbohydrate Chain Contained in Hela Cells and U937 Cells

Cultured Hela cells (human cervical cancer) and U937 cells (human systemicity lymphoma), which were respectively approximately one million cells, were washed with phosphate-buffered physiological saline (PBS) a few times to remove components derived from culture solutions. The cells were homogenized, and membrane fractions containing glycoprotein (glycoconjugate such as glycoprotein existing on surfaces of cell membranes) were collected according to a standard method known in the art. Then, the cells were solubilized by adding phosphate-buffered solution (50 μL) containing surfactant (NP-40) to the membrane fractions, and centrifuged. Further, with the clear supernatant (50 μL) obtained by the centrifugation, alkali decomposition was carried out to separate carbohydrate chains of glycoprotein, by means of the in-flow chemical reaction system illustrated in FIG. 1 in a substantially similar manner to the example 1. In the system, flow rate was 0.5 ml/min, a 0.5 M lithium hydroxide solution was used, and a reaction tube was 2.5 m in length, and reaction temperature was 70° C. (temperature in the thermostat layer).

After the alkali decomposition, O-linked carbohydrate chains contained in the collected reaction solution were labeled as 0.5 M 3-aminobenzoic acid derivatives, and excess reagent was removed by gel filtration. Then, the carbohydrate chains were analyzed by HPLC. HPLC analysis was carried out according to gradient method under the following conditions: a polymer-type amino column (Showa Denko K. K.; 4.0 mm×250 mm); eluent (5% acetic acid-2% triethylamine–10% acetonitrile mixed solvent); a flow rate of 1.0 ml/min; fluorescent detection (excitation wavelength 350 nm, fluorescence wavelength 425 nm).

Figure 9:
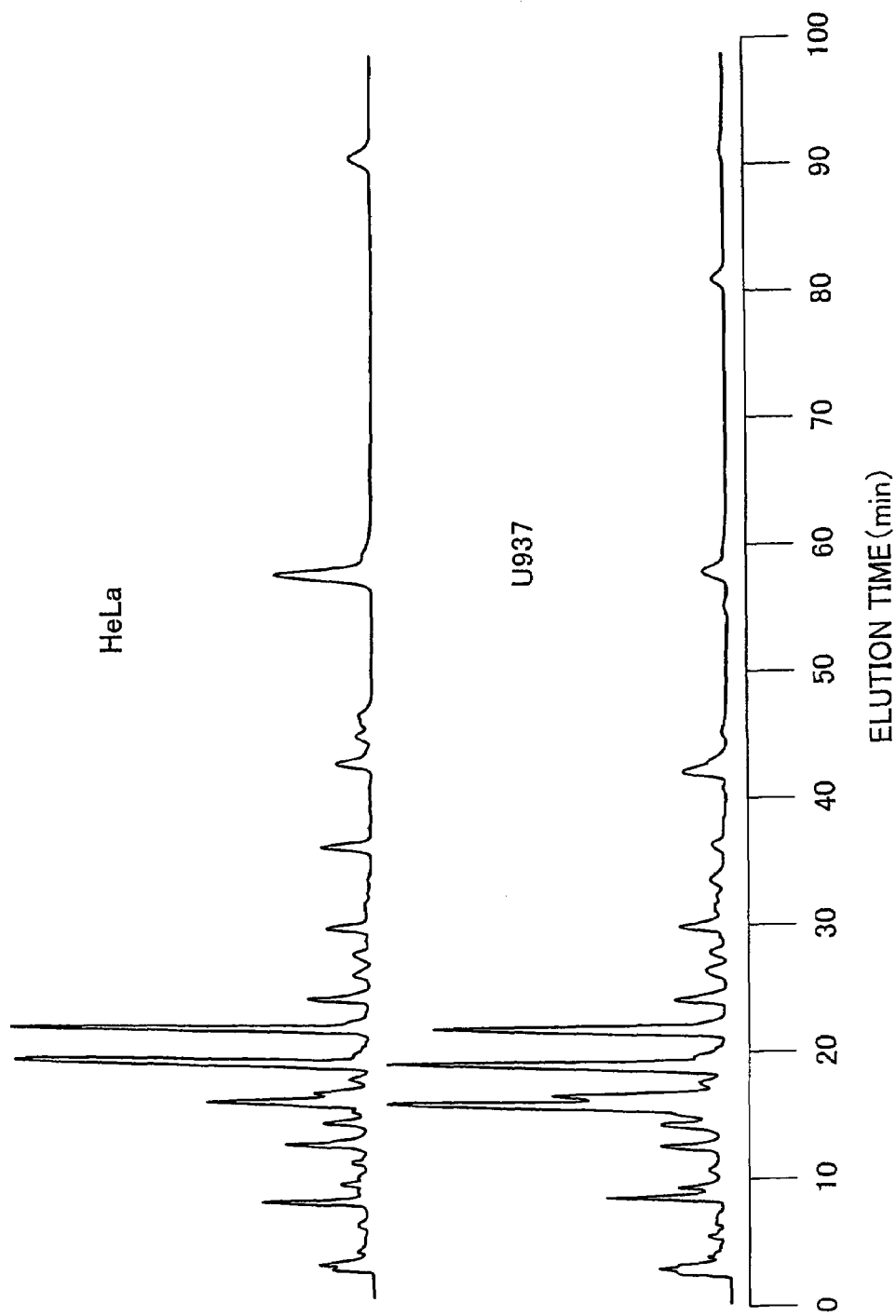
FIG. 9 is a graph showing results of analyzing O-linked carbohydrate chains separated from Hela cells and U937 cells by means of the in-flow chemical reaction system shown in FIG. 1, according to the example 2.

FIG. 9 is a graph showing results of analyzing O-linked carbohydrate chains in the Hela cells and the U937 cells. The analysis was carried out by using an amino column and examined carbohydrate chains obtained from the membrane fractions of the Hela cells and the U937 cells by the alkali decomposition of glycoprotein by using the in-line method and labeled with fluorescence. As shown in FIG. 9, between the Hela cells and the U937 cells, main carbohydrate chains are relatively similar, however, there is a difference in ratios of the carbohydrate chains. Therefore, even when carbohydrate chains or kinds of carbohydrate chains in the Hela cells and the U937 cells are similar, the cells can be evaluated based on a ratio of the carbohydrate chains.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, the present invention realizes separation of a carbohydrate chain from a glycoprotein in minutes, even though the separation has conventionally required one day or more. Thus, with many advantages described above, the present invention achieves significant rationalization and labor-saving in carbohydrate chain analysis, which is required for proteome analysis or proteomics in post genome, and achieves a high-precision analysis.

The invention claimed is:

1. An in-line flow-injection separation method for cleaving a glycoside linkage of a glycoconjugate that is contained in a sample solution, the separation method consisting essentially of the steps of:
   (i) introducing a sample solution of the glycoconjugate into an alkaline solution continuously passing in a flow path, thereby mixing the alkaline solution and sample solution;
   (ii) heating the mixed solution to a temperature in the range of 60° C. to 150° C., while the alkaline solution and the sample solution are flowing in the flow path, thereby cleaving the carbohydrate from the glycoconjugate;
   (iii) removing the alkaline solution from the mixed solution by passing the mixed solution through an ion-exchange column; and
   (iv) collecting the separated carbohydrate cleaved from the glycoconjugate;
   wherein a period for mixing the alkaline solution and the sample solution at the temperature in the range of 60° C. to 150° C. is within 3 minutes, and wherein the alkaline solution is at a concentration in the range of 0.1 to 2.0 M.

2. The in-line flow injection method for cleaving a glycoside from a glycoconjugate according to claim 1, wherein the glycoconjugate is a glycoprotein.

3. The in-line flow injection method for cleaving a glycoside from a glycoconjugate according to-claim 1, wherein, after a mixed solution of the alkaline solution and the sample solution is heated to a temperature in the range of 60° C. to 150° C., the mixed solution is cooled down to below 30° C.

4. The in-line flow injection method for cleaving a glycoside from a glycoconjugate according to claim 1, wherein the carbohydrate collected after cleavage from the glycoconjugate is labeled.

5. The in-line flow injection method for cleaving a glycoside from a glycoconjugate according to claim 2, wherein after the alkaline solution and the sample solution are heated to a temperature in the range of 60° C. to 150° C., the mixed solution is then cooled to below 30° C.

* * * * *